(12) United States Patent
Gitelman et al.

(10) Patent No.: US 6,572,063 B1
(45) Date of Patent: Jun. 3, 2003

(54) BRACKET FOR DENTAL FLOSS CONTAINER

(75) Inventors: Bruce J. Gitelman, Toronto (CA); Robert G. Dickie, Newmarket (CA)

(73) Assignee: Floss Today Corporation, Ontario (CA)

( * ) Notice: Subject to any disclaimer, the term of this patent is extended or adjusted under 35 U.S.C. 154(b) by 0 days.

(21) Appl. No.: 10/021,821

(22) Filed: Dec. 13, 2001

(51) Int. Cl.⁷ .................................................. A47F 5/00
(52) U.S. Cl. ................... 248/314; 248/205.3; 248/205.5
(58) Field of Search .............................. 248/314, 309.1, 248/205.3, 205.5, 300

(56) References Cited

U.S. PATENT DOCUMENTS

| | | |
|---|---|---|
| 4,881,560 A | 11/1989 | Blank et al. |
| 5,054,674 A | 10/1991 | Fortman |
| 5,076,423 A | 12/1991 | Russak |
| 5,156,311 A | 10/1992 | Spencer, Jr. et al. |
| 5,649,659 A | 7/1997 | Saunders |
| 6,095,465 A * | 8/2000 | Weck et al. ............. 248/205.3 |
| 6,126,129 A * | 10/2000 | Herron ..................... 248/311.3 |
| 6,318,689 B1 * | 11/2001 | Rodriguez ........... 248/205.5 X |

* cited by examiner

Primary Examiner—Ramon O. Ramirez
(74) Attorney, Agent, or Firm—Sand & Sebolt

(57) ABSTRACT

A bracket for removably supporting a dental floss container on a support surface is a one-piece plastic member having a back wall, a pair of spaced side walls with inturned end flanges and a bottom wall which form a pocket therebetween for slidably receiving and supporting the container therein. A pair of tapered ribs extend along the back wall for tilting an upper portion of the container forward to facilitate opening of a container lid. An adhesive strip on the back wall attaches the bracket to the support surface. In a second bracket embodiment a first part of a tongue and groove connection is formed on the front surface of the bracket and is adapted to mate with a second part of the tongue and groove connection formed on a back wall of the dental floss container to removably mount the container on the bracket.

21 Claims, 13 Drawing Sheets

US 6,572,063 B1

BRACKET FOR DENTAL FLOSS CONTAINER

BACKGROUND OF THE INVENTION

1. Technical Field

The invention relates to brackets, and in particular to a bracket for removably supporting a dental floss container on a support surface. Even more particularly, the invention relates to a bracket which removably mounts the dental floss container in the bracket in a position for easily dispensing dental floss therefrom without removing the container from the bracket.

2. Background Information

The use of dental floss has become an important product in dental hygiene and in the care of teeth. Dental floss comes in various types of dispensers to facilitate and encourage the use of the dental floss. The most common type of dental floss container includes a reel around which the dental floss is wound, wherein the reel is rotatably mounted within an outer protective housing or package. The container usually will include some type of cutting mechanism to facilitate cutting the dental floss after a predetermined length has been unwound from the reel. Many of these containers will have a rectangular outer housing with the cutting mechanism being mounted on one end thereof. Many of the containers will include a closure lid to maintain an exposed piece of the dental floss in a sanitary condition when not in use. Examples of some of these prior art dental floss containers are shown in U.S. Pat. Nos. 4,881,560, 5,054,674, 5,076,423, 5,156,311, and 5,649,659.

Although these dental floss containers work satisfactorily, it is believed important that the container be readily visible to the user to remind him/her to floss on a daily basis. However, most of these containers are usually stored in a drawer in the bathroom and since they are out of sight, do not serve as a reminder to regularly floss. It is believed that if the container is visible and conveniently located, for example, on the mirror or wall adjacent the washstand, that the user will floss more regularly than when the dental floss container is stored in a drawer out of sight. Thus, storing the dental floss container in a visible and readily accessibly location will serve as a reminder to the user to floss more regularly, especially if the dental floss container can be either removed from a supporting bracket for dispensing the floss therefrom or remain in the bracket when dispensing the dental floss from the storage reel.

BRIEF SUMMARY OF THE INVENTION

One aspect of the invention is to provide a bracket which can be conveniently attached to a supporting surface such as a wall or mirror, by various attachment devices, such as an adhesive strip or suction cup, which will removably hold a dental floss container.

A further feature of the invention is to provide such a dental floss container bracket which enables the dental floss to be removed from the container without removing the container from the supporting bracket, which will enable the container to have a protective closure lid to maintain the dental floss in a sanitary condition, and in which the lid can be opened and closed without removing the container from the supporting bracket.

Still another aspect of the invention is to provide such a supporting bracket which can be formed relatively inexpensively as a one-piece plastic member that is free of moving parts, yet which will slidably receive and hold a dental floss container therein, and which will enable the container to be easily removed each time the dental floss is dispensed therefrom or permit the container to remain in the bracket while the dental floss is being dispensed therefrom.

Another feature of the invention is to provide an extremely thin and compact bracket which is removably attached to a support surface by an adhesive strip or suction cup with the dental floss container being removably attached to the bracket as by a tongue and groove mounting arrangement.

A further aspect of the invention is to provide the bracket with tapered internal ribs which positions the top portion of the container far enough away from the supporting surface so that a container top lid can be opened sufficiently to provide access to the dental floss without moving the container from within the bracket further adding to the usability and cleanliness of the dispenser.

Still another aspect of the invention is to provide the bracket with an open front whereby the trademark of the manufacturer printed on the front of the dental floss container is viewable through the open front thereby enhancing its attractiveness to a dental floss manufacturer for supplying brackets with its dental floss containers to promote its product.

The foregoing advantages, construction, and operation of the present invention will become readily apparent from the following description and accompanying drawings.

BRIEF DESCRIPTION OF THE DRAWINGS

Preferred embodiments of the invention, illustrative of the best modes in which applicant contemplates applying the principles, are set forth in the following description and are shown in the drawings and are particularly and distinctly pointed out and set forth in the appended claims.

Similar numerals refer to similar parts throughout the drawings.

DETAILED DESCRIPTION OF THE INVENTION

Figure 1:
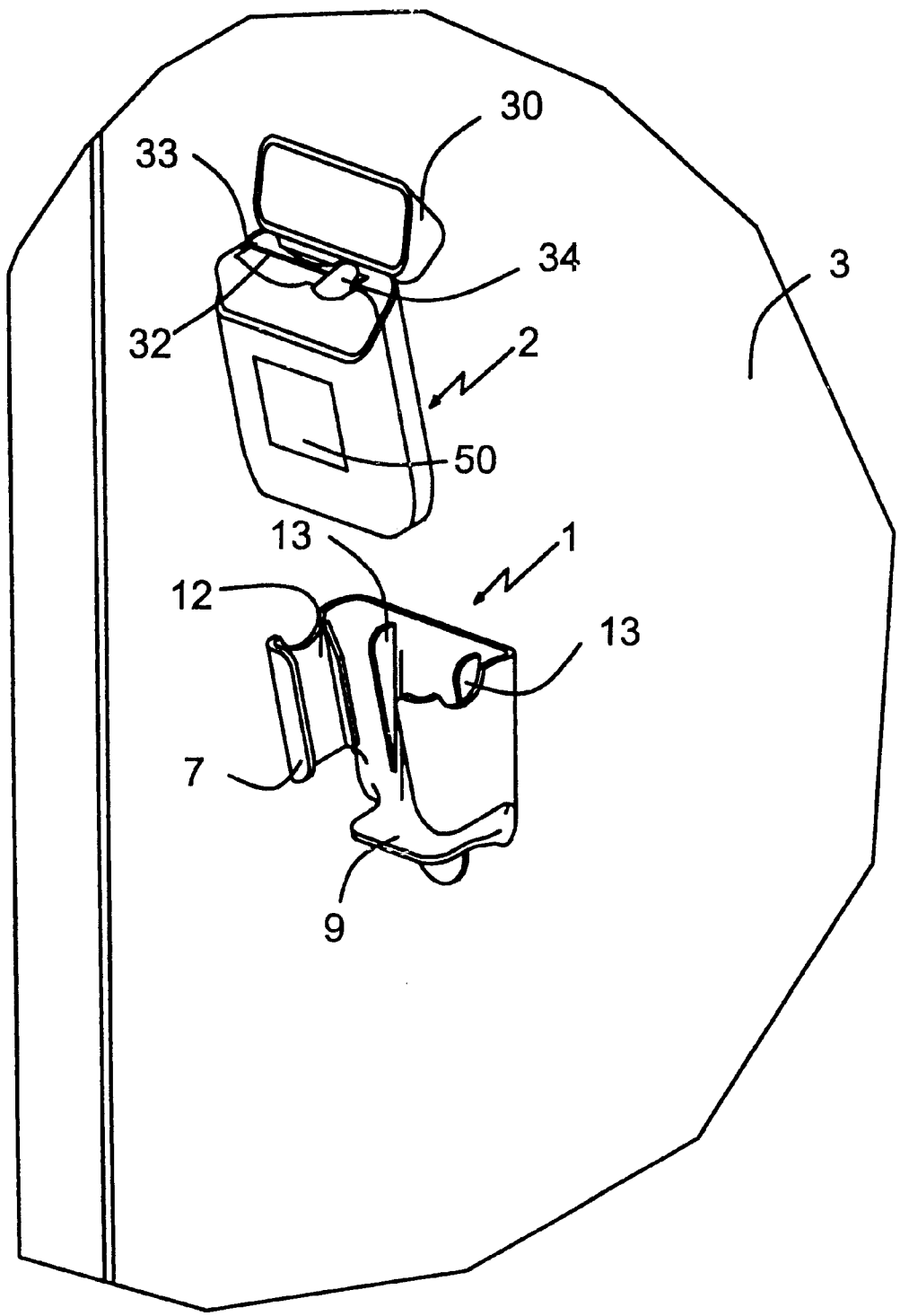
FIG. 1 is an exploded perspective view of a first embodiment of the dental floss bracket of the present invention in combination with a dental floss container.
Figure 2:
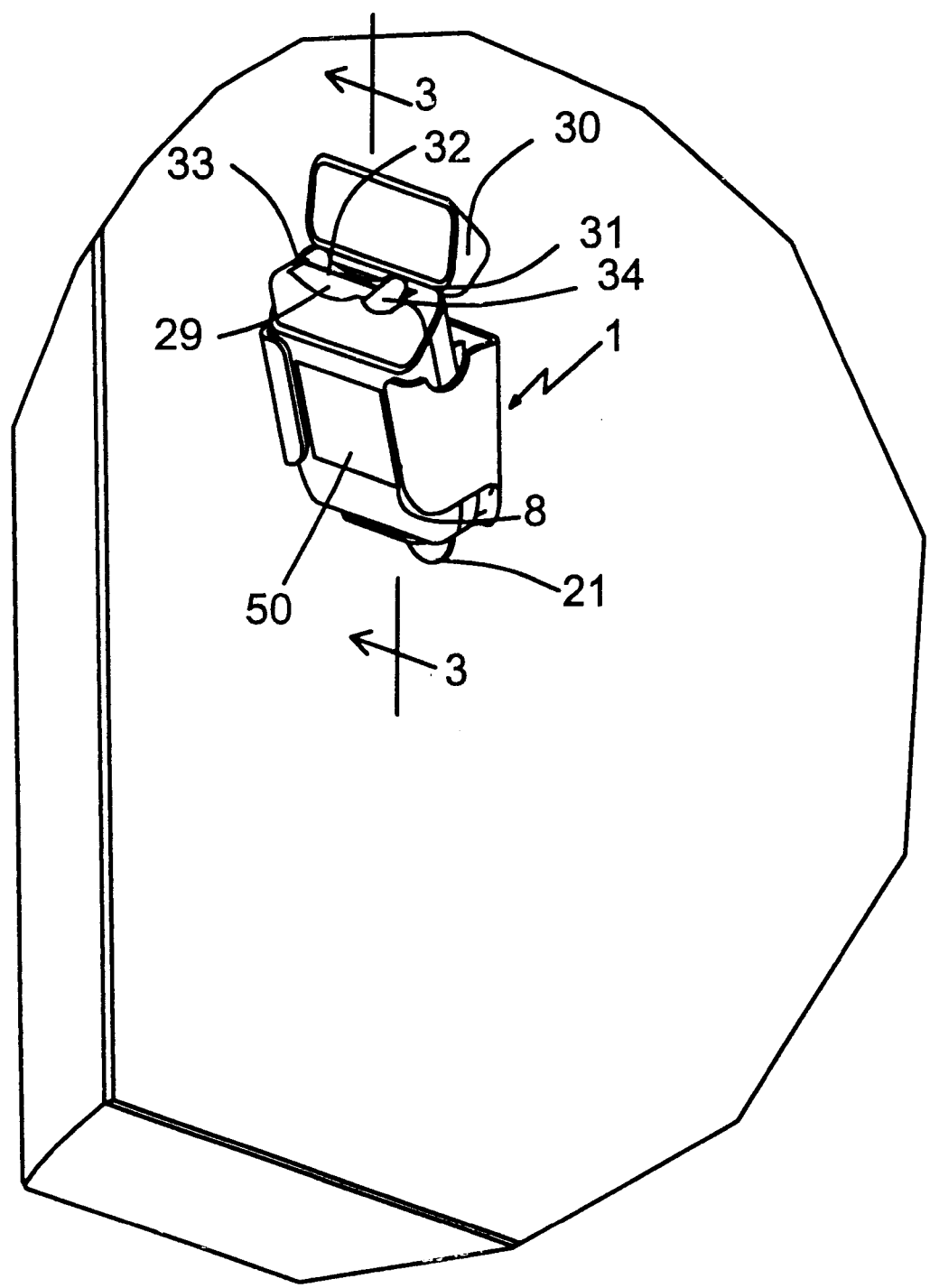
FIG. 2 is a perspective view showing the dental floss container being removably mounted within the bracket of the present invention which is mounted on a supporting surface.
Figure 3:
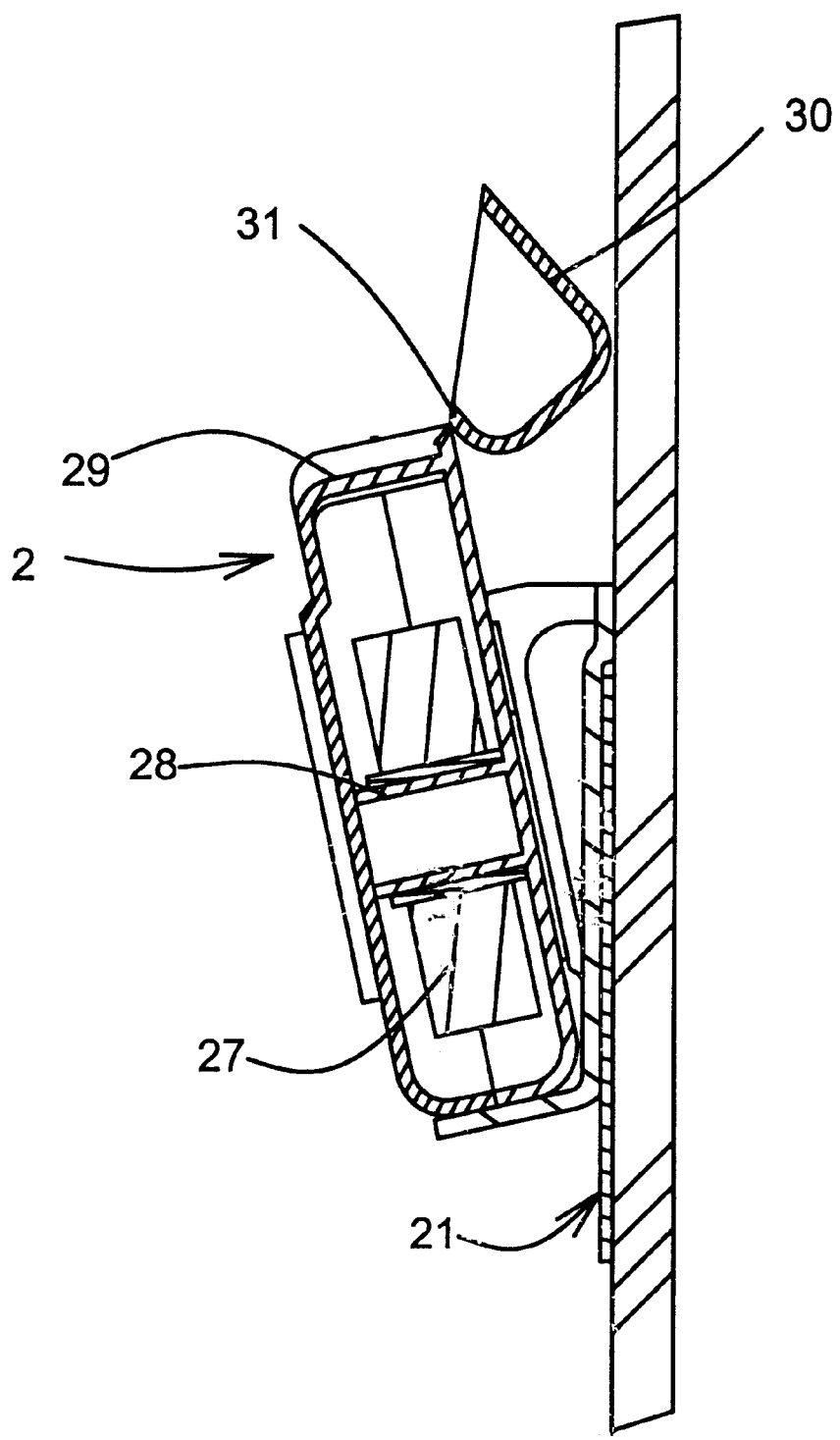
FIG. 3 is a sectional view taken on line 3—3, FIG. 2.
Figure 4:
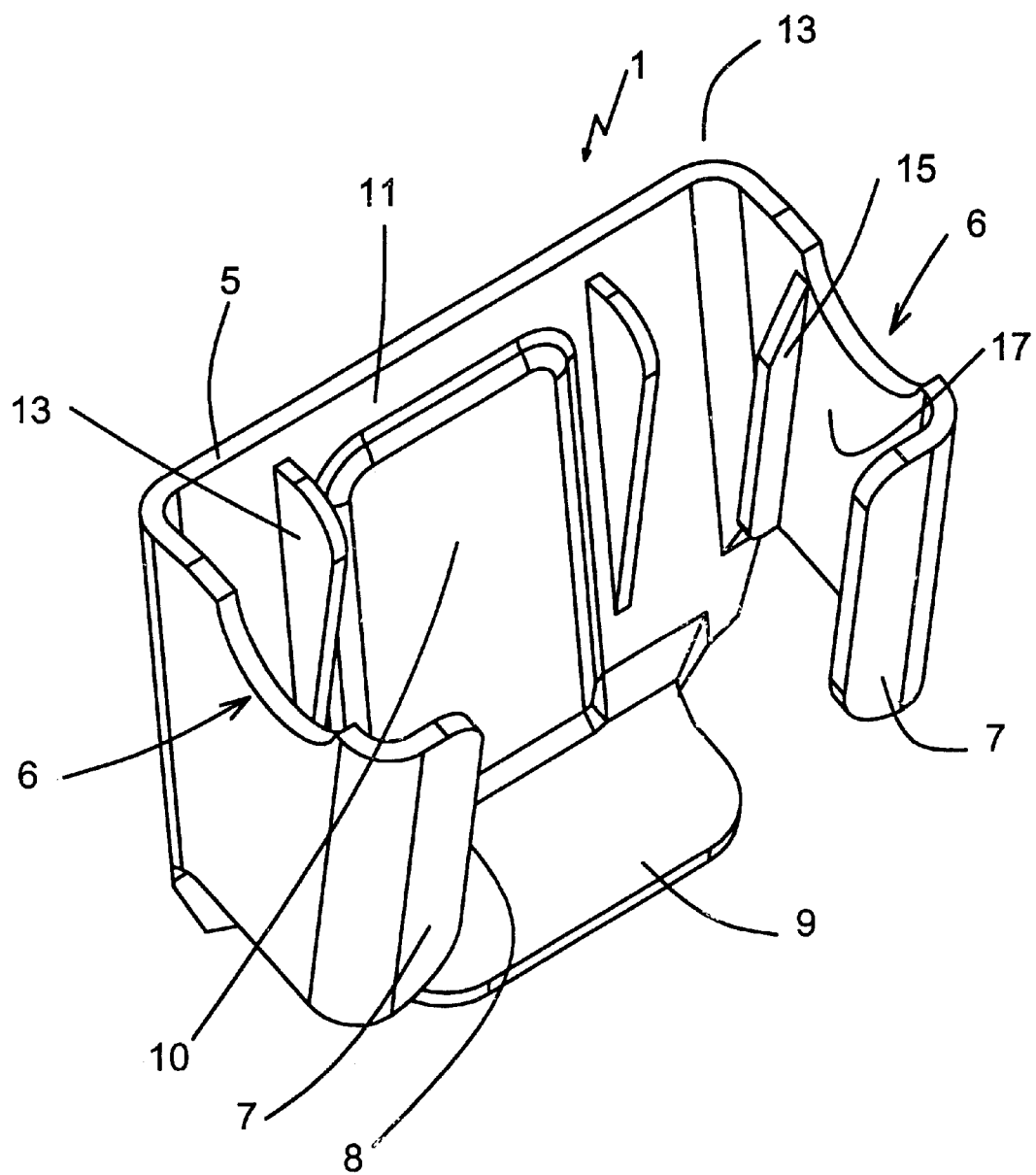
FIG. 4 is an enlarged front perspective view of the dental floss mounting bracket of the present invention.
Figure 5:
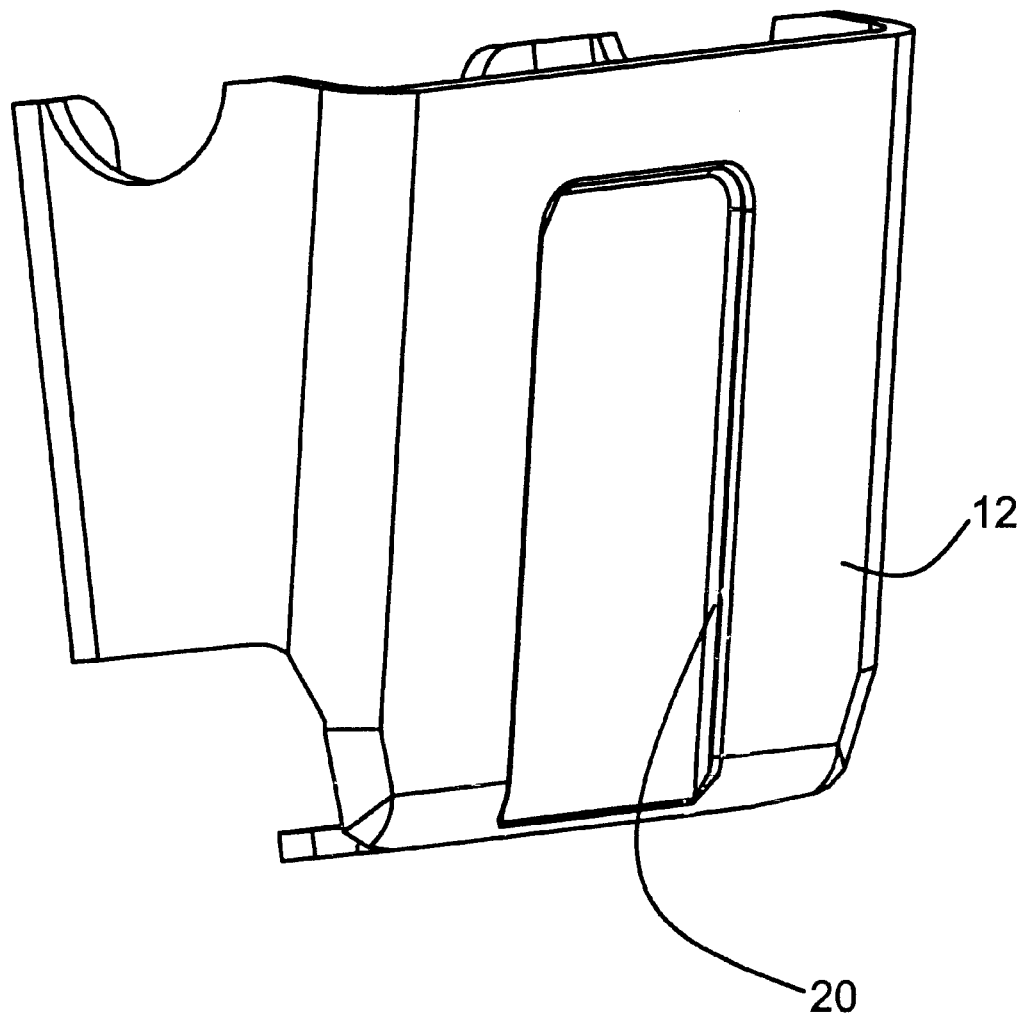
FIG. 5 is a back perspective view of the bracket.
Figure 6:
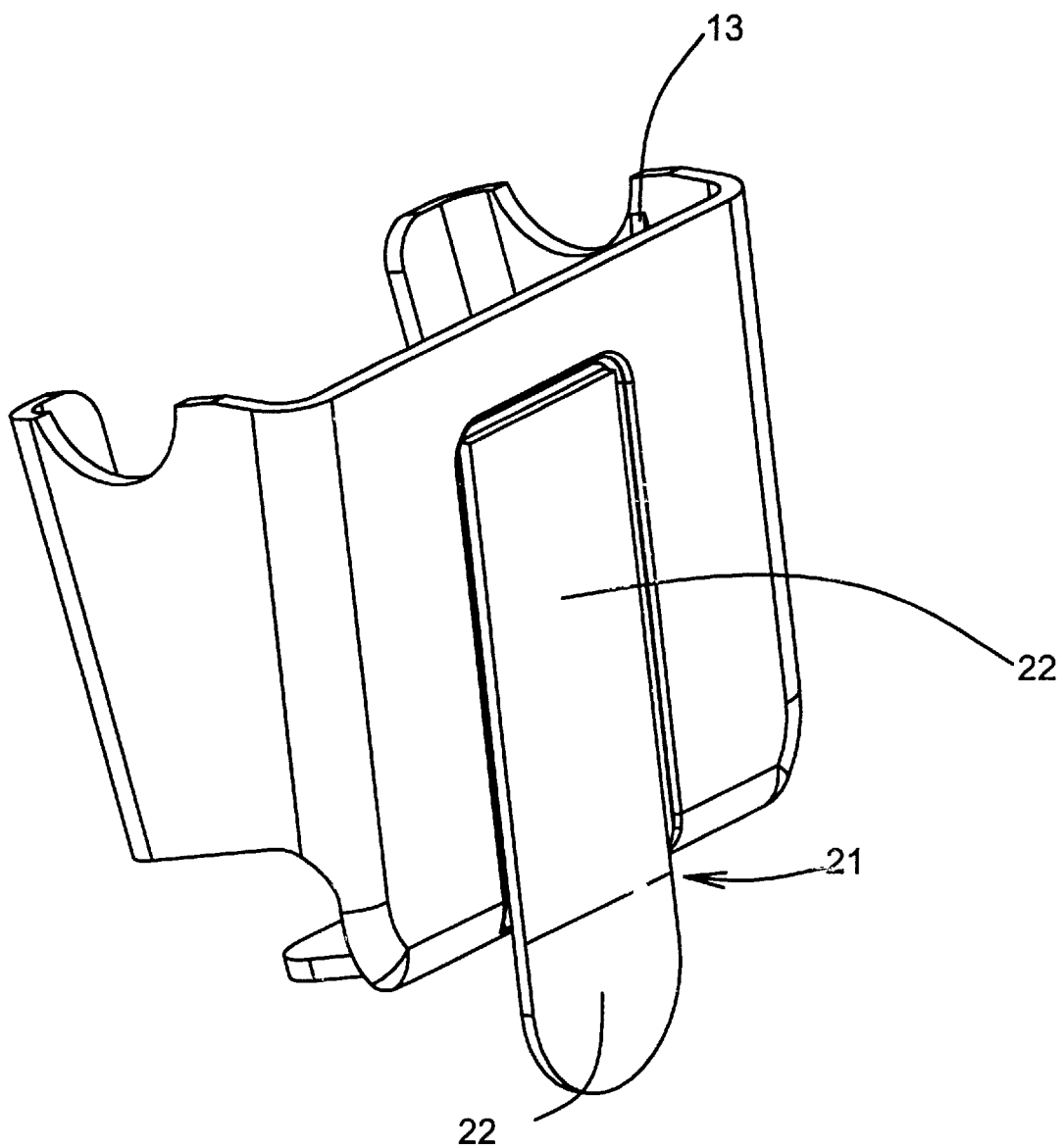
FIG. 6 is a perspective view similar to FIG. 5 showing an adhesive mounting strip attached to the back wall of the dental floss bracket.

The bracket of the present invention is indicated at 1, and is shown particularly in FIGS. 1–7. Bracket 1 is intended to removably mount a dental floss container indicated generally at 2, on a supporting surface 3 as shown in FIG. 2. As shown in FIGS. 4–6, bracket 1 is an integral one-piece member preferably formed of a plastic material, although it could be stamped of metal if desired. Bracket 1 includes a back wall 5, a pair of spaced sidewalls 6 which terminate in inwardly turned end flanges 7 which form an open front 8 therebetween. A bottom wall 9 extends outwardly from the lower end of back wall 5 and together with back wall 5 and sidewalls 6 form a pocket 10 for receiving container 2 therein. Back wall 5 includes front and rear surfaces 11 and 12 respectively, with a pair of downwardly tapered ribs 13 being formed on front surface 11. Another pair of opposed ribs 15 are formed on sidewalls 6 and are spaced inwardly from end flanges 7 to form a pair of spaced channels 17 therebetween for slidably receiving container 2 therein.

Figure 7:
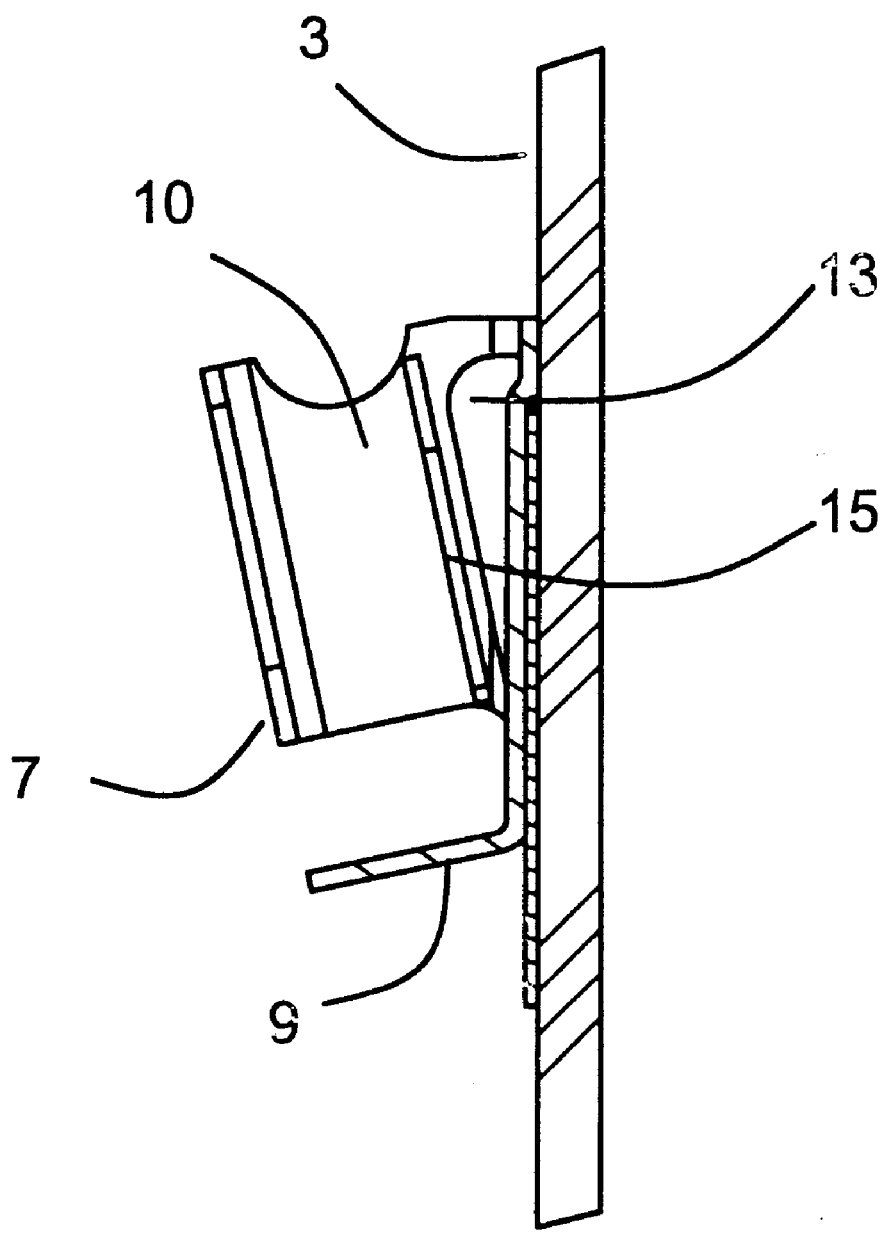
FIG. 7 is a side sectional view of the mounting bracket secured to a supporting surface by the adhesive strip of FIG. 6.

Bracket 1 may be attached by various attachments to support surface 3, one example of which is shown in FIGS. 5–7. An elongated channel 20 is formed in back wall 5 for receiving an adhesive strip indicated generally at 21. Adhesive strip 21 is a flexible flat plastic tape which has an adhesive coating on at least a portion of each of the two sides thereof. The coating on the surface adjacent channel 20 adheres the strip to bracket 1. The adhesive on surface 22 is provided with a release cover (not shown) whereby the bracket may be adhered to mounting surface 3 when desired, but not until ready for use. If desired, an uncoated portion 23 may be provided at the end of strip 21 to form a graspable tab which may be grasped by the fingers of the user to facilitate the removal of bracket 1 from mounting surface 3 in the future. A particular plastic tape having the characteristics as described above is marketed by 3-M Company under the trademark COMMAND. FIG. 7 shows bracket 1 being secured by adhesive strip 21 to supporting surface 3 with pocket 10 ready to slidably receive dental floss container 2 therein as shown in FIG. 2.

Figure 8:
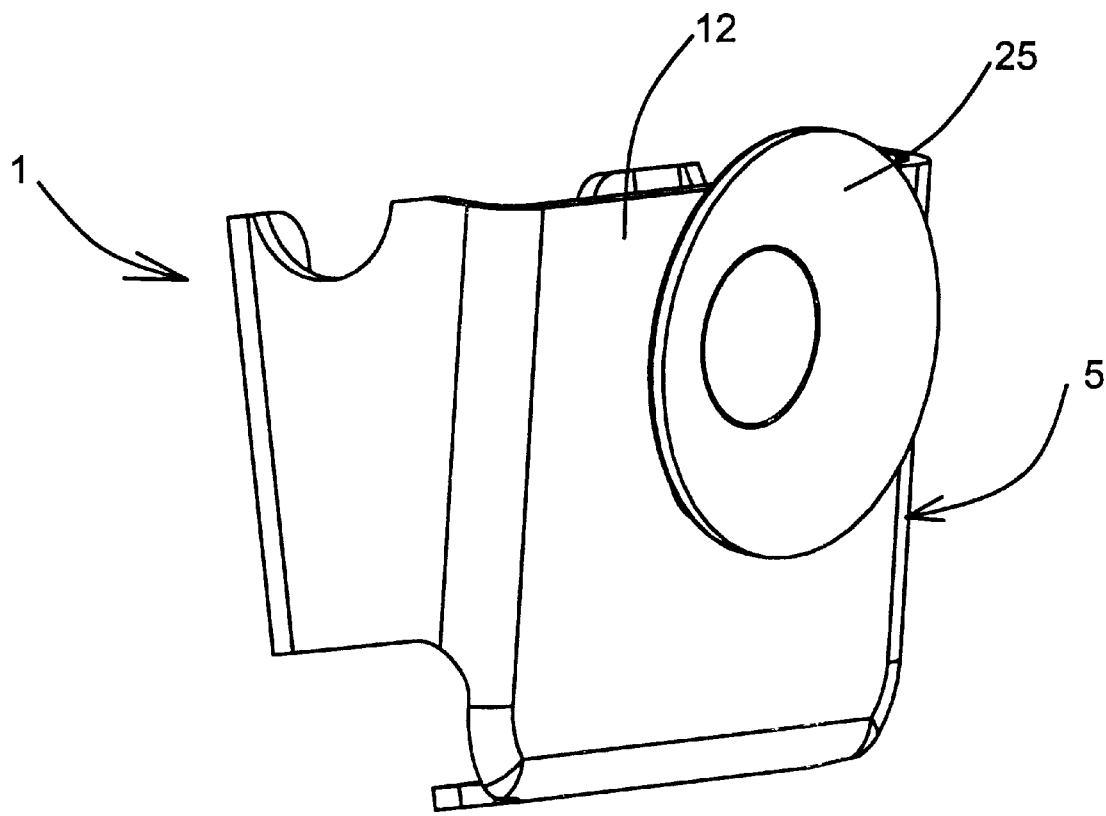
FIG. 8 is a back perspective view similar to FIG. 6, showing a suction cup mounted on the back wall of the bracket for securing it to a support surface.

Another type of attachment for securing bracket 1 on support surface 3 is shown in FIG. 8 in which a usual suction cup 25 is secured to rear surface 12 of back wall 5 for subsequently removably mounting bracket 1 on support surface 3.

One type of dental floss container 2 for use with bracket 1, has a rectangular shape with a roll of dental floss 27 (FIG. 3) being rotatably mounted within the container on a reel 28. Container 2 has an exposed top 29 enclosed by a lid 30 pivotally connected thereto by a hinge 31. A short section of dental floss 32 will extend from roll 27 through a top opening slot 33 to beneath a cutting device 34. This short section of dental floss 32 will be constantly exposed after a length of dental floss is removed and cut from roll 27 by device 34 for grasping by a user for the next flossing. Lid 30 enables the dental floss to be protected from outside contaminants. As shown in FIG. 3, ribs 13 due to their downwardly inwardly extending taper, will place container 2 at an angle whereby its upper end is spaced further from support surface 3 than its lower end enabling lid 30 to be moved to an open position for subsequent removal of a length of dental floss therefrom without removing container 2 from bracket 1. Thus, a user merely pivots lid 30 to the open position and removes the desired length of floss from roll 27 and by movement of the floss in a particular direction, will sever it from the roll by cutting device 34. This procedure can be accomplished with one hand afterwhich lid 30 is moved to a closed position maintaining the exposed strip 32 of dental floss free from contaminants. Container 2 is securely retained within bracket 1 by its mounting in slide channels 17 between ribs 15 and end flanges 7 while being supported on bottom wall 9 in a tilted position by ribs 13.

Figure 9:
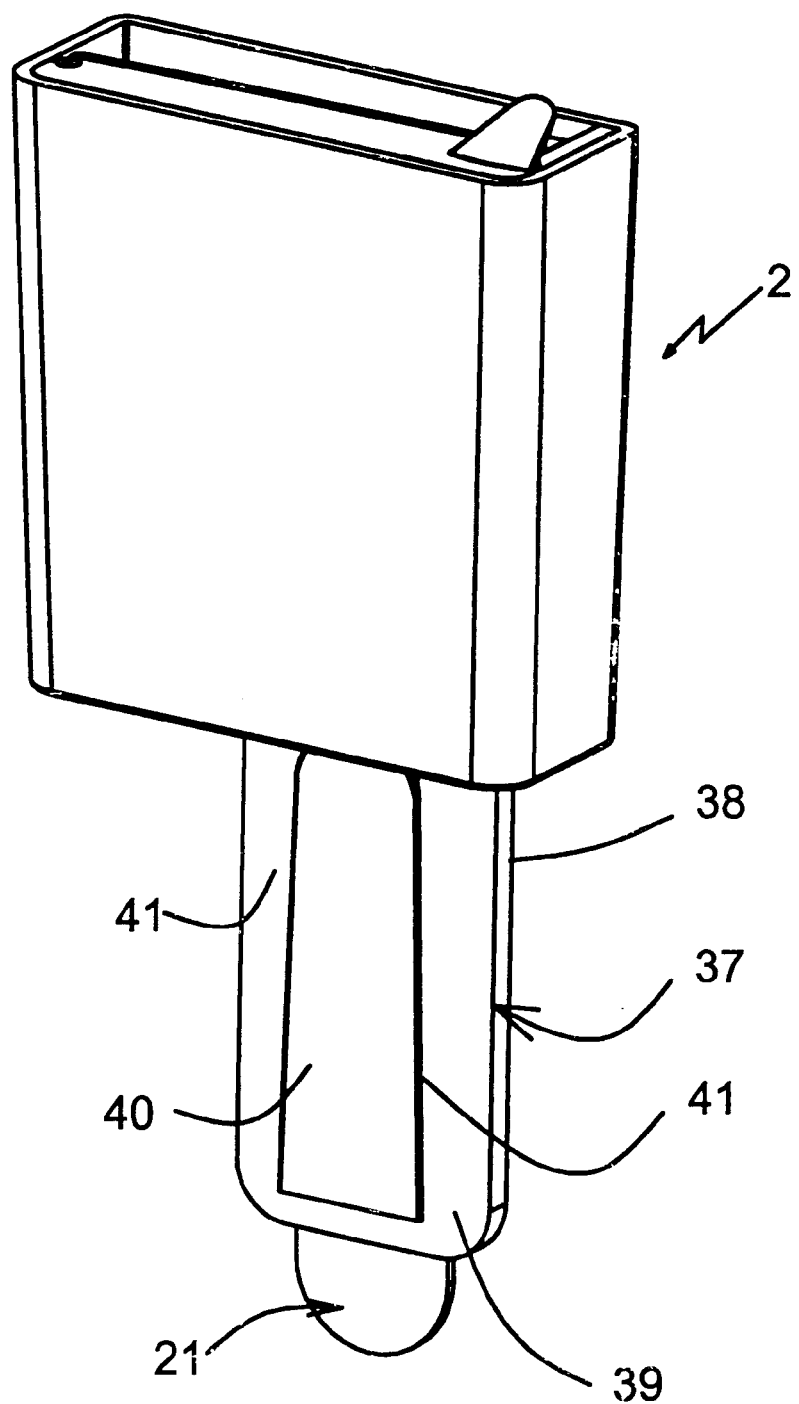
FIG. 9 is a front perspective view showing a second embodiment of the bracket having a tongue and groove connection for removably mounting a dental floss container on the bracket.
Figure 10:
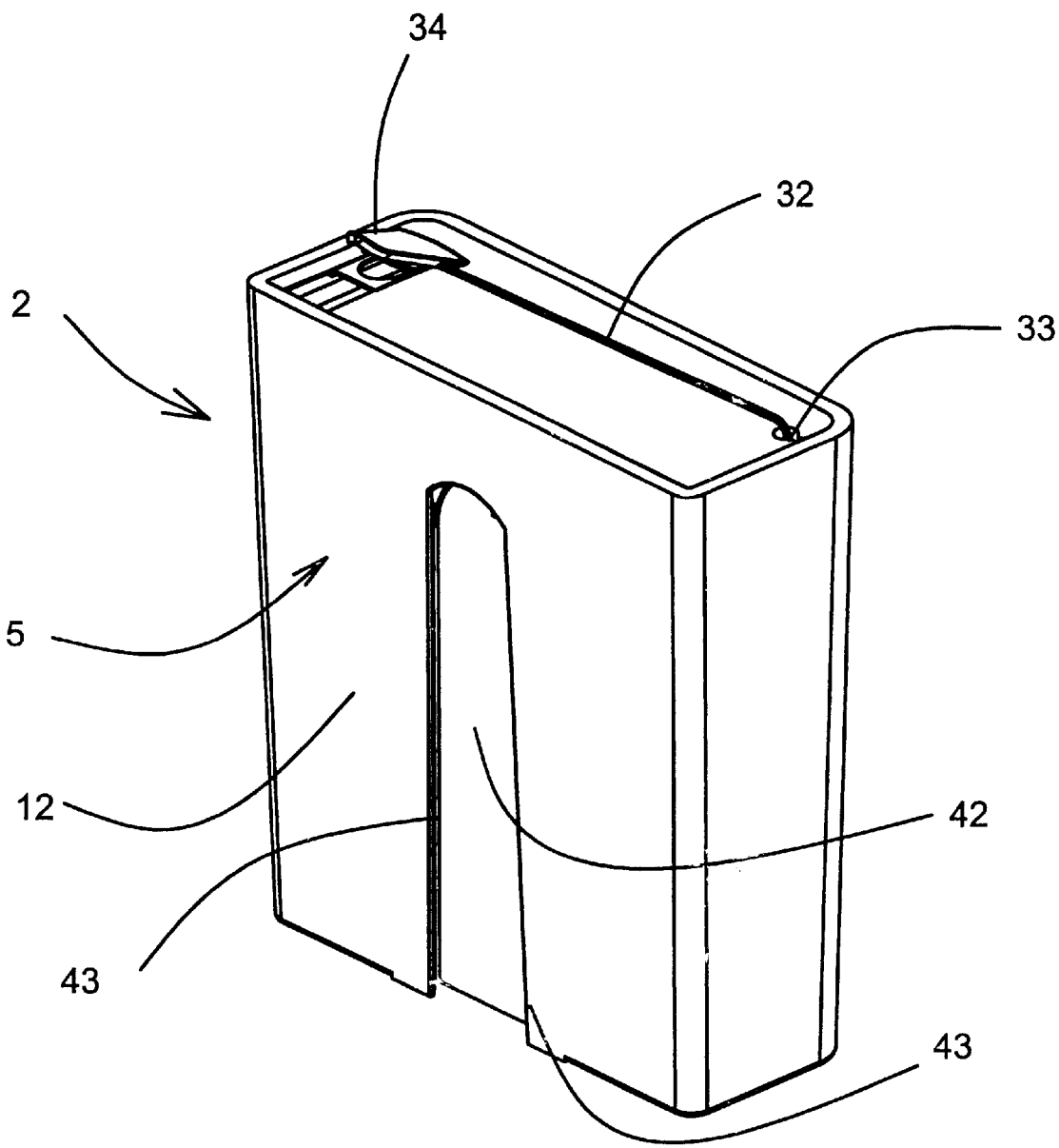
FIG. 10 is a back perspective view of the dental floss container of FIG. 9 having one portion of the tongue and groove connection formed in the back wall thereof.
Figure 11:
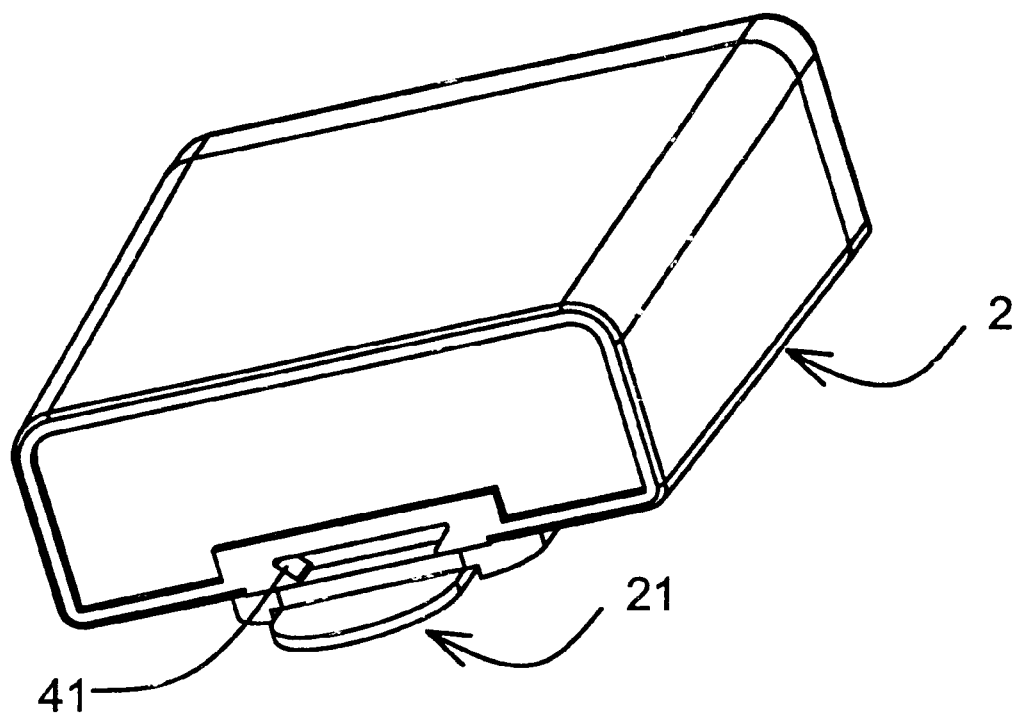
FIG. 11 is a bottom perspective view showing the mounting of the dental floss container on the modified bracket by the tongue and groove connection shown in FIGS. 9 and 10.

A modified bracket for supporting a dental floss container on a support surface is indicated generally at 37, and is shown in FIGS. 9–11. Bracket 37 is an elongated generally flat strip of rigid material such as plastic, and has a pair of planar surfaces 38 and 39. A strip of pressure sensitive adhesive which can be similar to adhesive strip 21 described above, is applied to surface 39. One component of a tongue and groove connection such as the tongue 40, is formed integrally on bracket 37 and extends outwardly from surface 39, providing a pair of spaced inwardly tapered surfaces 41 extending along the sides thereof as in the usual tongue and groove connection. The rear surface 12 of container 2 will be formed with the other component of a tongue and groove connection which will include a channel 42 defined by a pair of tapered undercut sides 43 which are complementary to and slidably engageable with the tapered side surfaces 41 of tongue 40. Thus, flat bracket 37 is secured to support surface 3 by adhesive strip 21 or other attachment as discussed above, and dental floss container 2 is slidably mounted thereon by engagement of tongue 40 within channel 42 formed in the back surface of container 2. Thus, this provides a mounting bracket which is considerably smaller and more compact than bracket 1, which is able to removably mount dental floss container 2 thereon, so long as the back wall 5 thereof has been configured with one of the components of a tongue and groove connection.

Figure 12:
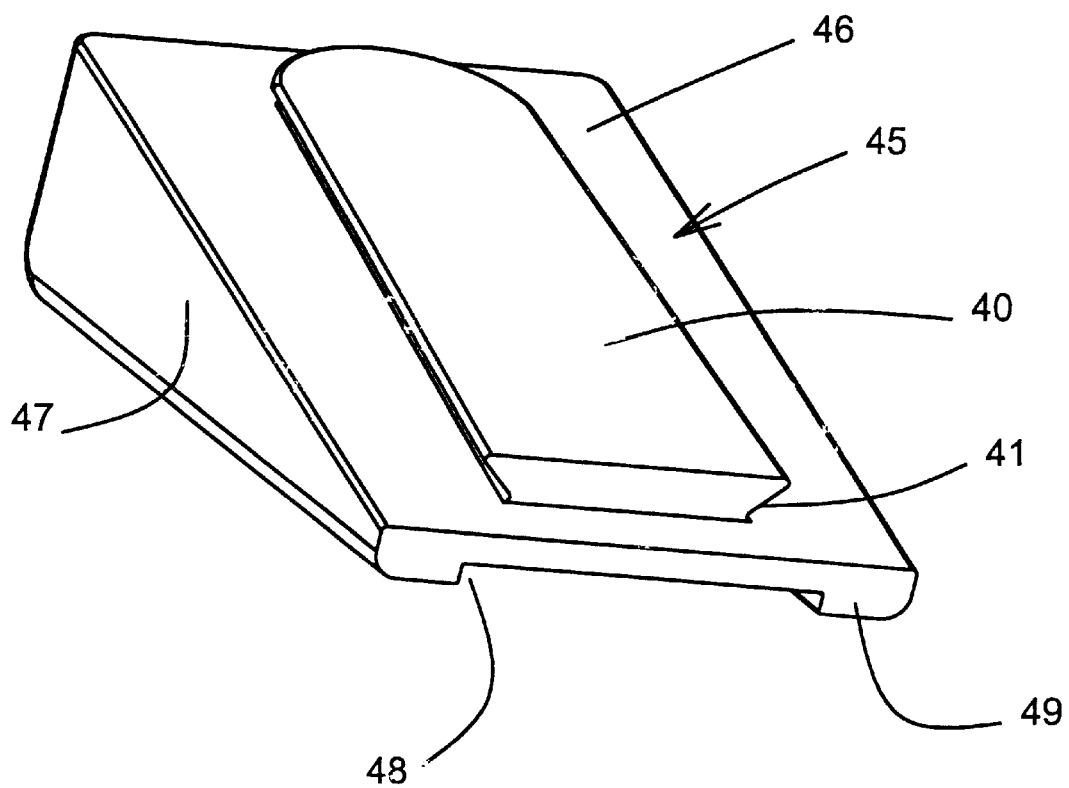
FIG. 12 is a perspective view of a further modified bracket having one portion of the tongue and groove connection formed thereon.
Figure 13:
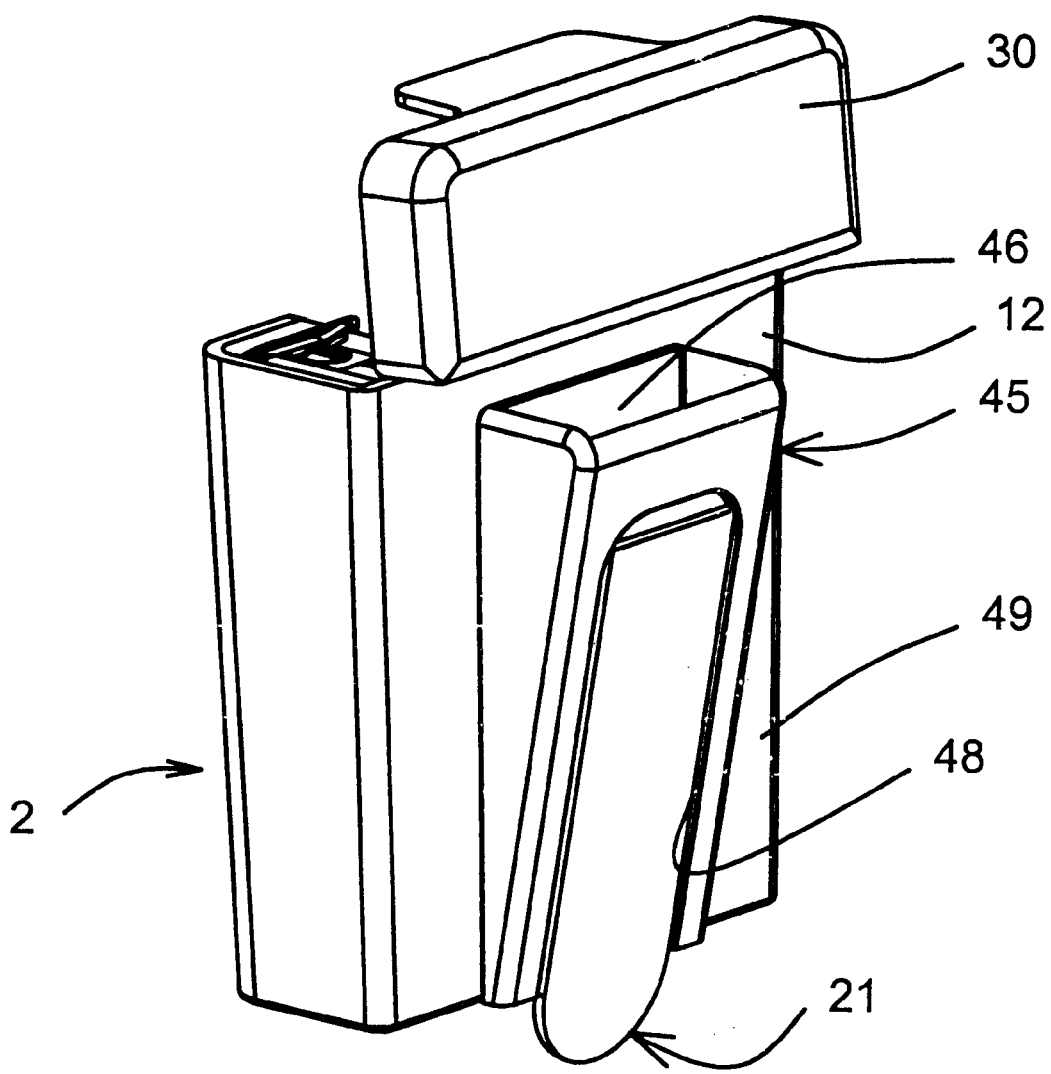
FIG. 13 is a back perspective view showing the bracket of FIG. 12 attached to a back wall of a dental floss container by the tongue and groove connection.

A slightly modified tongue and groove bracket is shown in FIGS. 12 and 13 and is indicated generally at 45. Bracket 45 is similar in many respects to bracket 37 discussed above in that it has a tongue 40 and the undercut side surfaces 41 formed integrally on an inner wall 46 thereof. The main difference is that bracket 45 has triangularly-shaped sidewalls 47 which extend outwardly from wall 46 so that a back surface 49 extends at an angle with respect to wall 46. A channel 48 is formed in back wall 49 of bracket 45 for receiving an adhesive strip 21 therein for mounting bracket 45 on a support surface, which in turn, is adapted to slidably receive and mount container 2 thereon by the tongue and groove connection formed on bracket 45 and in the rear surface of container 2.

Bracket 45 provides for the spacing of the upper portion of container 2 from the supporting structure in a similar manner as shown in FIG. 3, to enable lid 30 to be pivoted to the open position for removal of a strip of dental floss therefrom without removing container 2 from bracket 45. Thus, when bracket 45 and container 2 are joined together by the tongue and groove connection as shown in FIG. 13 and mounted on a support surface by adhesive 21, it will assume a position similar to that shown in FIG. 3 which provides the necessary clearance for the pivotal opening movement of lid 30.

Again, brackets 1 and 45 enable a user to remove a strip of dental floss with only one hand by merely opening the lid and pulling the desired length of dental floss from within the container and by movement of the dental floss in a certain direction across cutting device 34, will cut the desired length of dental floss without disturbing the container other then the opening and closing movement of the lid. This similar action is used with bracket 37 which need not be tilted outwardly from the support surface if the container does not have a lid. Again, the brackets can be placed closely adjacent a wash basin or at any desired location by attaching the bracket to the support surface by adhesive strip 21, suction cup 25, or other type of attachment. Again, the dental floss container is easily removed and replaced with a new dental floss container upon exhaustion of the dental floss stored therein.

In accordance with another feature of the invention, a manufacturer's logo indicated at 50 in FIGS. 1 and 2, is easily seen through open front 8 of bracket 1 which is desirable to the dental floss manufacturer. Likewise, all of the advertising logo is readily visible on dental floss container 2 when used with brackets 37 and 45 since the front and sides of the container are completely exposed when mounted on the brackets.

Thus, the improved mounting bracket of the present invention is an extremely simple and inexpensive device which can be mass produced of light-weight durable plastic requiring only the use of an adhesive strip, suction cup, or other attachment for mounting the bracket on a support surface at a desired location for removably mounting a dental floss container therein, which enables the user to remove a strip of dental floss with only one hand, and in which a protective lid can be used on the container to maintain the exposed dental floss in a sanitary condition.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

What is claimed is:

1. A bracket adapted to be mounted on a support surface for removably supporting a dental floss container therein, said bracket comprising:
   a back wall having front and rear surfaces;
   an attachment mounted on the back wall for mounting the bracket on a support surface;
   a support formed on the front surface of the back wall for removably supporting the dental floss container on said bracket;
   the support including a pair of spaced side walls and a bottom wall formed integrally with and extending outwardly from the back wall and forming a pocket therebetween for slidably receiving and retaining the dental floss container therein; and
   at least one projection being formed on the back wall and extending into the pocket for spacing an upper portion of the dental floss container from the back wall.

2. The bracket defined in claim 1 wherein the back wall, side walls, and bottom wall are formed as an integral one-piece plastic member.

3. The bracket defined in claim 1 wherein the attachment is an adhesive strip.

4. The bracket defined in claim 3 wherein the adhesive strip is a flexible plastic tape having an adhesive coating on at least a portion of each of two sides thereof.

5. The bracket defined in claim 4 wherein said flexible plastic tape is stretchable, and wherein a second portion on each of the two sides thereof has no adhesive coating thereon; and wherein the uncoated portion of the flexible plastic tape forms a graspable tab to facilitate removal of the bracket from the support surface when adhered thereto.

6. The bracket defined in claim 1 wherein the attachment is a suction cup.

7. A bracket adapted to be mounted on a support surface for removably supporting a dental floss container therein, said bracket comprising:
   a back wall having front and rear surfaces;
   an attachment mounted on the back wall for mounting the bracket on a support surface;
   a support formed on the front surface of the back wall for removably supporting the dental floss container on said bracket;
   the support including a pair of spaced side walls and a bottom wall formed integrally with and extending outwardly from the back wall;
   the sidewalls terminating in inturned end flanges; and
   a rib formed on each of the sidewalls and spaced from the inturned end flanges to form a channel therebetween for slidably receiving the dental floss container therein.

8. The bracket defined in claim 7 wherein the attachment is an adhesive strip.

9. A bracket adapted to be mounted on a support surface for removably supporting a dental floss container therein, said bracket comprising:
   a back wall having front and rear surfaces;
   an adhesive strip mounted on the back wall for mounting the bracket on a support surface;
   a support formed on the front surface of the back wall for removably supporting the dental floss container on said bracket; and
   a channel formed in the rear surface of the back wall, the adhesive strip being mounted in said channel.

10. A bracket adapted to be mounted on a support surface for removably supporting a dental floss container therein, said bracket comprising:
    a back wall having front and rear surfaces;
    an attachment mounted on the back wall for mounting the bracket on a support surface;
    a support formed on the front surface of the back wall for removably supporting the dental floss container on said bracket;
    the support including a pair of spaced side walls and a bottom wall formed integrally with and extending outwardly from the back wall and forming a pocket therebetween for slidably receiving and retaining the dental floss container therein; and
    the back wall including a pair of spaced ribs formed on the front surface of the back wall and tapering inwardly and downwardly toward the bottom wall.

11. The bracket defined in claim 10 wherein the back wall, side walls, and bottom wall are formed as an integral one-piece plastic member.

12. A bracket adapted to be mounted on a support surface for removably supporting a dental floss container therein, said bracket comprising:
    a back wall having front and rear surfaces;
    an attachment mounted on the back wall for mounting the bracket on a support surface;
    a support formed on the front surface of the back wall for removably supporting the dental floss container on said bracket; and the front surface support being one component of a tongue and groove connection.

13. The bracket defined in claim 12 wherein the attachment is an adhesive strip.

14. In combination a dental floss container and a bracket for removably supporting said container on a support surface, said bracket comprising:

a back wall having front and rear surfaces;

an attachment mounted on the back wall for mounting the bracket on the support surface;

a support formed on the front surface of the back wall for removably supporting the dental floss container on said bracket;

the support including a pair of spaced side walls and a bottom wall formed integrally with and extending outwardly from the back wall and forming a pocket therebetween for slidably receiving and retaining the dental floss container therein; and at least one projection being formed on the back wall and extending into the pocket for spacing an upper portion of the dental floss container from the back wall.

15. The combination defined in claim 14 wherein the attachment is a suction cup.

16. The combination defined in claim 14 wherein the container has a generally rectangular configuration with a pivotally mounted lid on one side thereof.

17. The combination defined in claim 14 wherein the attachment is an adhesive strip.

18. In combination a dental floss container having a back wall and a bracket for removably supporting said container on a support surface, said bracket comprising:

a back wall having front and rear surfaces;

an attachment mounted on the bracket back wall for mounting the bracket on the support surface;

a support formed on the front surface of the bracket back wall for removably supporting the dental floss container on said bracket; and the support being a first component of a tongue and groove connection and a second component of the tongue and groove connection being formed on the back wall of the container.

19. The bracket defined in claim 18 wherein the back wall is inclined to space an upper portion of the container from the support surface.

20. In combination a dental floss container and a bracket for removably supporting said container on a support surface, said bracket comprising:

a back wall having front and rear surfaces;

an attachment mounted on the back wall for mounting the bracket on the support surface;

a support formed on the front surface of the back wall for removably supporting the dental floss container on said bracket;

the support including a pair of spaced side walls and a bottom wall formed integrally with and extending outwardly from the back wall;

the sidewalls terminating in inturned end flanges; and a rib formed on each of the sidewalls adjacent the back wall and spaced from the end flanges to form a channel therebetween for slidably receiving the dental floss container therein.

21. The bracket defined in claim 20 wherein the back wall, side walls, and bottom wall are formed as an integral one-piece plastic member.

* * * * *